United States Patent [19]

Archibald et al.

[11] 4,177,279
[45] Dec. 4, 1979

[54] 1-[(3-INDOLYL)-ALKYL]-PIPERIDYL UREAS AND HYPOTENSIVE COMPOSITIONS

[75] Inventors: John L. Archibald, Windsor; John L. Jackson, Royston, both of England

[73] Assignee: John Wyeth & Brother Ltd., Taplow, England

[21] Appl. No.: 597,841

[22] Filed: Jul. 21, 1975

Related U.S. Application Data

[63] Continuation-in-part of Ser. No. 511,415, Oct. 2, 1974, abandoned.

[30] Foreign Application Priority Data

Oct. 10, 1973 [GB] United Kingdom ............... 47208/73
Jan. 25, 1974 [GB] United Kingdom ............... 03531/74
Feb. 18, 1974 [GB] United Kingdom ............... 07277/74

[51] Int. Cl.² .................. A61K 31/445; C07D 401/06
[52] U.S. Cl. .......................... 424/267; 260/326.12 R; 260/326.16; 546/201; 546/212; 546/214; 546/224; 546/244; 546/273
[58] Field of Search ............... 260/293.61; 424/267; 546/201

[56] References Cited

U.S. PATENT DOCUMENTS

| 3,183,235 | 5/1965 | Zenitz | 260/294 |
| 3,217,011 | 11/1965 | Zenitz | 260/294.3 |
| 3,527,761 | 9/1970 | Archibald et al. | 260/293 |
| 3,655,674 | 4/1972 | Archibald | 260/293.61 |

Primary Examiner—John M. Ford
Assistant Examiner—Richard A. Schwartz
Attorney, Agent, or Firm—Arthur E. Wilfond

[57] ABSTRACT

The invention provides compounds of general formula I

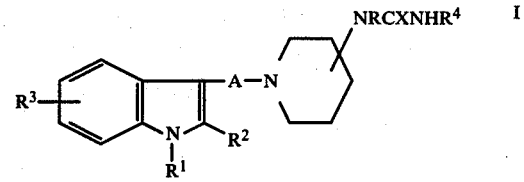

and pharmaceutically acceptable acid addition and quaternary ammonium salts thereof, wherein R represents hydrogen or lower alkyl, $R^1$ represents hydrogen or lower alkyl, $R^2$ represents hydrogen or lower alkyl, $R^3$ represents hydrogen, halogen, lower alkoxy, hydroxy, or lower alkyl, $R^4$ represents hydrogen, lower alkyl, cycloalkyl of 5 to 7 carbon atoms, thienyl, furyl, phenyl; phenyl mono- or disubstituted by halogen, lower alkyl, lower alkoxy, hydroxy or trifluoromethyl; or benzoyl, halobenzoyl, lower alkanoyl, cycloalkanoyl of 6 to 8 carbon atoms, or thienoyl, A represents an alkylene, mono- or diketo- or hydroxy-alkylene radical having from 1 to 5 carbon atoms and X is oxygen or sulphur.

The compounds exhibit action on the cardiovascular system particularly hypotensive and/or anti-hypertensive activity.

18 Claims, No Drawings

1-[(3-INDOLYL)-ALKYL]-PIPERIDYL UREAS AND HYPOTENSIVE COMPOSITIONS

RELATED APPLICATIONS

This application is a continuation-in-part of application Ser. No. 511,415, filed Oct. 2, 1974, now abandoned.

DESCRIPTION OF THE INVENTION

The invention relates to novel indole derivatives to processes for preparing them and to pharmaceutical compositions containing them.

The present invention provides compounds of the general formula:

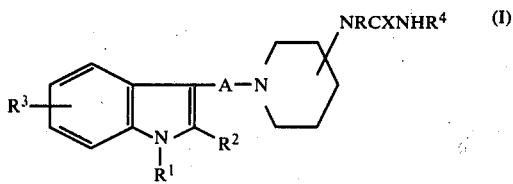

and pharmaceutically acceptable acid addition and quaternary ammonium salts thereof, wherein R represents hydrogen or lower alkyl, $R^1$ represents hydrogen or lower alkyl, $R^2$ represents hydrogen or lower alkyl, $R^3$ represents hydrogen, halogen, lower alkoxy, hydroxy, or lower alkyl, $R^4$ represents hydrogen, lower alkyl, cycloalkyl of 5 to 7 carbon atoms, thienyl, furyl, phenyl; phenyl mono- or disubstituted by halogen, lower alkyl, lower alkoxy, hydroxy, or trifluoromethyl; or benzoyl, halobenzoyl, lower alkanoyl, cycloalkanoyl of 6 to 8 carbon atoms or thienoyl, A represents an alkylene, mono- or diketo- or hydroxy-alkylene radical having from 1 to 5 carbon atoms and X represents oxygen or sulphur.

The term "lower" in relation to alkyl and alkoxy radicals used herein means that the radical contains from 1 to 6 carbon atoms. Usually such radicals containing from 1 to 4 carbon atoms are preferred.

The alkylene radicals A may be straight chain or branched and when A is branched it is preferably a straight chain alkylene containing up to 4 carbon atoms in the chain and carrying one methyl substituent. A may be for example —CH₂—, —CH₂CH₂—, —CH₂CH₂CH₂—, —CH₂CH₂CH₂CH₂—,

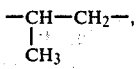

—CO(CH₂)₃— or —CHOH(CH₂)₃— but is preferably CH₂—CH₂.

Examples of lower alkyl radicals for R, $R^1$, $R^2$, $R^3$ or $R^4$ are methyl, ethyl, n-propyl, isopropyl, n-butyl and isobutyl.

$R^4$ when heteroaryl can be thienyl e.g. 2-thienyl or furyl, e.g. 2-furyl.

Substituted phenyl radicals which can be used for $R^4$ include phenyl substituted by one or two substituents chosen from halogen such as chlorine, fluorine or bromine, lower alkoxy such as methoxy or ethoxy, lower alkyl such as methyl or ethyl, hydroxy, or trifluoromethyl.

Lower alkoxy radicals for $R^3$ include methoxy, ethoxy, propoxy and butoxy.

Cycloalkyl radicals for $R^4$ are cyclopentyl, cyclohexyl and cycloheptyl.

The radical $R^4$ when acyl may be benzoyl, halobenzoyl, lower alkanoyl of 2 to 7 carbon atoms e.g. acetyl or propionyl, or cycloalkanoyl of 6 to 8 carbon atoms e.g. cyclohexanoyl, or thienoyl, e.g. 2-thienoyl.

Preferred compounds of formula I are those in which $R^1$, $R^2$ and $R^3$ are hydrogen, those in which $R^4$ is phenyl, 2-trifluoromethylphenyl, benzoyl, cyclohexanoyl or thienoyl, those in which R is hydrogen or methyl and those in which A is —CH₂CH₂—

Specific preferred compounds of the invention are:

1-phenyl-3-[1-(2-[indolyl]ethyl)piperid-4-yl] urea;

1-[1-(2-[3-indolyl]ethyl) piperid-4-yl]-3-[2-trifluoromethylphenyl] urea;

1-benzoyl-3-[1-(2-[3-indolyl]ethyl) piperid-4-yl] urea;

1-phenyl-3[1-(2-[3-indolyl]ethyl) piperid-4-yl] thiourea,

1-[1-(2-[3-indolyl]ethyl)piperid-4-yl]-1-methyl-3-phenyl urea 1-cyclohexanoyl-3-[1-(2-[3-indolyl] ethyl)-piperid-4-yl] urea 1-(2-thienoyl)-3-[1-(2-[3-indolyl]-ethyl)-piperid-4-yl] urea 1-[1-(2-[3-indolyl]ethyl)piperid-4-yl]-1-methyl-3-phenyl thiourea 1-[1-(2-[3-indolyl]ethyl)piperid-4-yl]thiourea and their pharmaceutically acceptable acid addition salts.

The acid addition salts of the compounds of formula I which are within the scope of the invention include those formed from inorganic and organic acids in particular pharmaceutically acceptable acid addition salts such as the sulphate, hydrochloride, hydrobromide, hydro-iodide, nitrate, phosphate, sulphonate (such as the methane sulphonate and p-toluene sulphonate), acetate, maleate, fumarate, tartrate and formate salts.

The quaternary ammonium salts include those formed with alkyl halides (e.g. methyl bromide or chloride) and aralkyl halides (e.g. benzyl bromide or chloride).

The compounds of formula I exhibit pharmacological activity namely action on the cardiovascular system (particularly hypotensive and/or anti-hypertensive activity).

The compounds of formula I may be prepared in a number of ways by building up the molecule from suitable starting materials in known manner. Such processes applied to the preparation of the novel compounds of formula I are included in the scope of the invention.

The preferred method for preparing compounds of formula I comprises reacting a compound of formula II

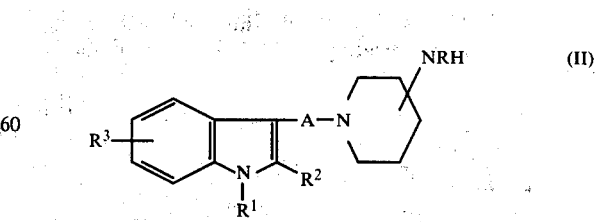

(wherein R, $R^1$, $R^2$, $R^3$ and A are as defined in connection with formula I) with a compound of formula III

$$R^4N=C=X \quad (III)$$

wherein $R^4$ is as defined in connection with formula I except hydrogen and X is oxygen or sulphur. When X is oxygen compound III is an isocyanate ($R^4$NCO,IIIa) and when X is sulphur compound III is an isothiocyanate ($R^4$NCS,IIIb).

If A contains a carbonyl group this reaction should be conducted under mild conditions to avoid the possibility of reaction between the amine II (when R is hydrogen) and the carbonyl group of another molecule of amine II giving a Schiffs base. This does not apply when the carbonyl group is adjacent to the piperidine nitrogen since it does not then behave as a ketone group. Usually the reaction to form the compound of formula I takes place at room temperature.

The starting materials of formula II wherein R is hydrogen may be prepared by methods described in our British Specification No. 1,218,570. The starting materials of formula II wherein R is lower alkyl may be prepared by alkylating corresponding compounds of formula II wherein R is hydrogen, or by methods analogous to those described in British Specification No. 1,218,570.

Compounds of formula I wherein R is hydrogen may be prepared by hydrolysis of the corresponding compounds of formula I where $R^4$ is acyl e.g. benzoyl or halobenzoyl.

A second method for preparing compounds of formula I comprises reacting a compound of formula (IV)

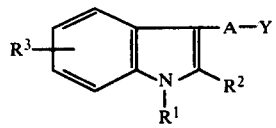

(IV)

wherein $R^1$, $R^2$, $R^3$, and A are as defined in connection with formula I, and Y is a halogen atom or an equivalent replaceable atom or radical for example an organic sulphonyl radical such as a tosyl radical, with a compound of formula (V)

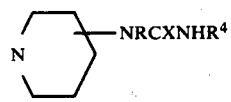

(V)

wherein R, $R^4$ and X are as defined in connection with formula I.

Compounds of formula IV may be prepared as described in British Specification No. 1,218,570. Compounds of formula (V) may be prepared by known methods.

A third method of preparing the compounds of formula I comprises reacting a compound of formula

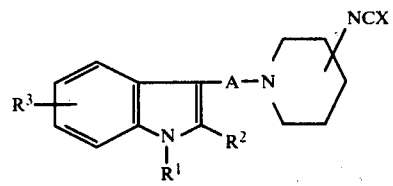

(VII)

(wherein $R^1$, $R^2$, $R^3$, X and A are as defined in connection with formula I) with an amine of formula $R^4$NH$_2$ (X) wherein $R^4$ is as defined in connection with formula I except hydrogen and acyl.

When A contains a carbonyl group care should be taken to avoid reaction between the amine (X) and the carbonyl group except when the carbonyl group is adjacent to the piperidine nitrogen. Compounds of formula (VII) (wherein neither A nor $R^3$ contain a hydroxy group and X is sulphur) may be prepared by reacting an amine of formula II wherein R is hydrogen either with (a) thiophosgene then calcium oxide or (b) carbon disulphide followed by ammonia to form a compound of formula IX

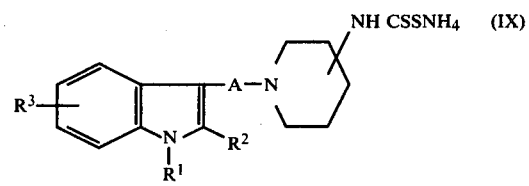

which is then treated with a heavy metal salt MB$_2$, wherein M is a divalent heavy metal and B$_2$ is two monovalent or one divalent anion. Examples of MB$_2$ are Cu SO$_4$, Pb Co$_3$, Fe SO$_4$ and Pb(NO$_3$)$_2$.

Compounds of formula VII wherein X is oxygen and neither A nor $R^3$ contain a hydroxy group may be prepared by treatment of a compound of formula II, wherein R is H with phosgene followed by treatment of the product with calcium oxide according to the following reaction scheme:

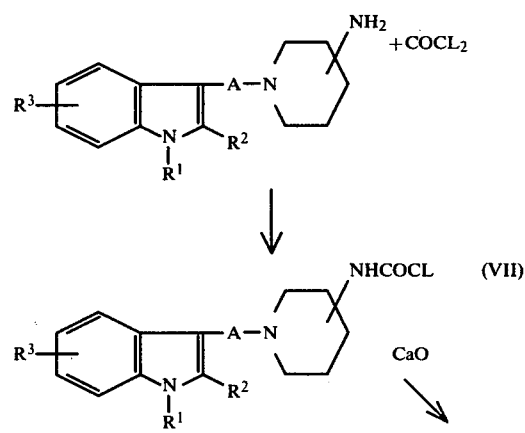

If a compound of formula I is prepared in which the chain A contains one or more carbonyl functions, then this chain may be selectively reduced e.g. with an alkali-metal borohydride, except when the carbonyl group is adjacent to the piperidine nitrogen. Thus the COCH$_2$ residue may be reduced with sodium borohydride to give the —CH(OH)CH$_2$— residue. When X is oxygen a compound of formula I wherein A contains one or more carbonyl functions may be reduced by a hydride transfer agent (particularly lithium aluminium hydride). Thus the oxalyl residue COCO may be reduced under mild conditions to the —CH(OH)CH$_2$— residue or under more drastic conditions to the —CH$_2$CH$_2$— residue.

A further method for preparing compounds of formula I, comprises reducing a corresponding compound of formula (VI) or (VIa)

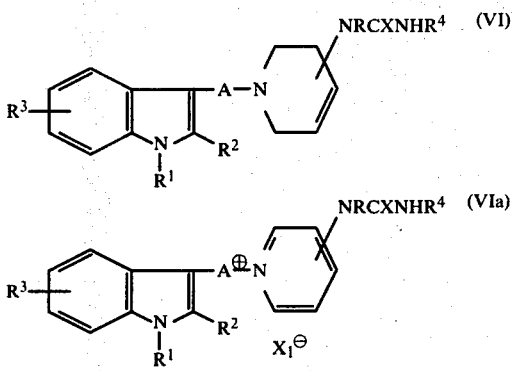

wherein R, R¹, R², R³, R⁴, and A are as defined in connection with formula I and $X_1^-$ is an anion e.g. a halide ion.

A compound of formula (VIa) may be reduced with an alkali metal borohydride e.g. sodium borohydride to give a corresponding compound of formula (VI). Compounds of formula VIa or VI (wherein X is oxygen) may also be reduced by catalytic hydrogenation e.g. in the presence of Raney nickel or a platinum catalyst to a corresponding compound of formula I.

Another method of preparing compounds of formula I wherein X is oxygen and A is an alkylene radical comprises reacting a compound of formula (VIIa)

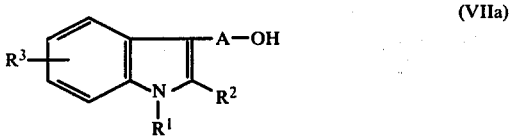

wherein R¹, R² and R³ are as defined in connection with formula I and A is an alkylene radical, with a compound of formula (V) as defined above wherein X is oxygen.

The reaction is preferably carried out in the presence of a catalyst, for example Raney nickel. An organic solvent, which is inert under the reaction conditions, is usually used for example xylene, toluene or benzene. Preferably the reaction is carried out by heating the reactants under reflux in a water-immiscible organic solvent, for example xylene, and removing the water formed during the reaction by azeotropic distillation. If necessary, reactive substituent groups can be blocked during a reaction and released later.

Compounds of formula (I) wherein X is oxygen may also be prepared by treating a compound of formula (VIII)

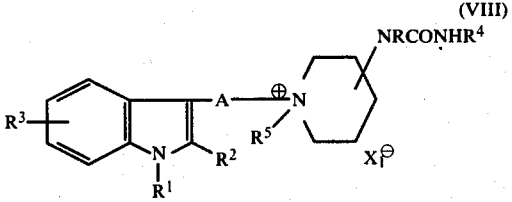

wherein R, R¹, R², R³, R⁴ and A are as defined in connection with formula I and R⁵ is an aryl methyl radical and $X_1^-$ is an anion e.g. a halide ion, under mild conditions such as to remove the group R⁵. Preferably the group R⁵ is removed by hydrogenolysis under standard conditions e.g. using an appropriate catalyst such as a palladium on carbon catalyst, a platinum catalyst or a nickel catalyst. In this reaction a mono or diketo lower alkylene radical A may also be reduced to a corresponding hydroxy lower alkylene radical A. If the keto compound is desired it can be obtained by oxidation of the final product.

Instead of a compound of formula (VIII) wherein R⁵ is as defined above any other starting material where R⁵ is an organic group which can be readily removed under mild conditions can be used.

Other conditions which may be effective to remove the group R⁵ are treatment with acid e.g. with acetic acid or hydrochloric acid to remove a trityl group or treatment with alkali metal in liquid ammonia.

Examples of groups R⁵ in the starting materials of formula (VIII) are arylmethyl radicals such as benzyl, diphenylmethyl, trityl or naphthlmethyl, benzyl being preferred.

A method for preparing compounds of formula (I) wherein R⁴ is hydrogen and X is oxygen comprises reacting a compound of formula (II) with nitrourea ($H_2NCONH.NO_2$).

Once a compound of general formula (I) has been prepared, then if necessary one or more substituents in the molecule may be converted to another substituent within its own meanings specified in connection with formula (I).

When a compound of formula (I) is produced wherein the R³ represents lower alkoxy or aryl-lower alkoxy hydrolysis or dealkylation to the corresponding hydroxyl compound may be brought about in known manner.

A further method for preparing compounds of formula (I) wherein R⁴ is an acyl radical namely benzoyl, halobenzoyl, lower alkanoyl, cycloalkanoyl of 6 to 8 carbon atoms or thienoyl comprises reacting a compound of formula I wherein R⁴ is hydrogen with the appropriate acylating agent such as an acid chloride or bromide.

If necessary, in any of the reactions hereinbefore described, reactive substituent groups may be blocked during a reaction and released at a later stage.

The invention also includes pharmaceutical compositions containing as active ingredient an active compound of formula I as above defined. The active compound may be micronised if desired. In addition to the active ingredient, the compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient.

Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxy-methyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

The following examples illustrate the invention. Temperatures are in °C.

EXAMPLE 1

1-Phenyl-3-[1-(2-[3-indolyl]ethyl piperid-4-yl]urea

To a solution of 3-8 2-(4-aminopiperidyl)ethyl]indole hydrate (1.31 g.) in warm dry benzene (125 ml.), was added phenyl isocyanate (0.63 g. 5% excess) in benzene (25 ml.).

The mixture was stirred at room temperature overnight and the title compound (1.74 g.) was filtered off. This was converted to the hydrochloride (1.39 g.) m.p. 214°–219° in ethanol-HCl/ether.

$C_{22}H_{26}N_4O$ HCl $\frac{1}{2}H_2O$ requires C, 64.77; H, 6.92; N, 13.74 Found: C, 64.69; H, 6.91; N, 13.45%

The product exhibited very good hypotensive activity and also anti-hypertensive activity.

EXAMPLE 2

1-(4-Chlorophenyl)-3-[1-(2-[3-indolyl]ethyl)piperid-4-yl]urea

Condensation of 3-[2-(4-aminopiperidyl)ethyl]indole, hydrate (1.05 g.) and 4-chlorophenyl isocyanate (0.65 g., 5% excess) in the manner of Example (1), gave the crude title compound (1.55 g.) from which a pure hydrochloride hemi-hydrate (1.41 g, m.p. 244.4° (dec.)) was obtained by treatment with ethanolic HCl/ether.

$C_{22}H_{25}ClN_4O.HCl. \frac{1}{2}H_2O$ requires: C, 59.72; H, 6.15, N, 12.66 Found: C, 60.02; H, 6.33; 12.36%

The product exhibited antihypertensive activity.

EXAMPLE 3

1-[3,4-Dichlorophenyl]-3-[1-(2-[3-indolyl]ethyl)piperid-4-yl] urea.

Condensation of 3-[2-(4-aminopiperidyl)ethyl]indole, hydrate (1.31 g.) and 3,4-dichlorophenyl isocyanate (0.99 g., 5% excess) in the manner of Example 1 gave the crude title compound (2.03 g.) from which a pure hydrochloride (1.70 g., m.p. 258.4°, dec.) was obtained by treatment with ethanolic HCl/ether.

$C_{22}H_{24}Cl_2N_4O$ HCl requires: C, 56.48; H, 5.39; N, 11.98. Found: C, 56.69; H, 5.53; N, 11.84%.

The product exhibited hypotensive activity.

EXAMPLE 4

1-[1-(2-[3-Indolyl]ethyl)piperid-4-yl]-3-[4-methoxyphenyl]urea

Condensation of 3-[2-(4-Aminopiperidyl)ethyl]indole, hydrate (1.31 g.) and 4-methoxyphenyl isocyanate (0.78 g., 5% excess) in the manner of Example 1 gave the crude title product (1.86 g.) from which a pure hydrochloride, hydrate (1.96 g., 220.4°, dec.) was obtained by treatment with ethanolic HCl/ether.

$C_{23}H_{28}N_4O_2$. HCl. $H_2O$ requires C, 61.81; H, 6.99; N, 12.53. Found: C, 62.22; H, 6.84; N, 12.40%

The product exhibited hypotensive and antihypertensive activity.

EXAMPLE 5

1-[1-(2-[3-Indolyl]ethyl)piperid-4-yl]-3-[3-tolyl]urea

Condensation of 3-[2-(4-Aminopiperidyl)ethyl]indole, hydrate (1.31 g.) and 3-tolyl isocyanate (0.70 g., 5% excess) in the manner of Example 1 gave the crude title compound (1.70 g.) from which was obtained a pure hydrochloride (1.57 g., m.p. 228.9°, dec.) by treatment with ethanolic HCl/ether.

$C_{23}H_{28}N_4O$ HCl requires: C, 66.93; H, 7.08; N, 13.57. found: C, 67.01; H, 7.21; N, 13.66%

The product exhibited hypotensive activity.

EXAMPLE 6

1-[1-(2-[3-Indolyl]ethyl)piperid-b 4-yl]-3-[2,6-dimethylphenyl] urea

Using the procedure of Example 1 4-amino-1-[2-(3-indolyl) ethyl]piperidine, hydrate (1.307 g) and 2,6-dimethylphenyl isocyanate (0.688 g., 25% excess) gave the title compound as the hydrochloride (1.110 g, 52%) m.p. 329.7° (dec).

$C_{24}H_{30}N_4O.HCl$ requires: C, 67.53; H, 7.32; N, 13.12. Found: C, 67.55; H, 7.50; N, 12.63%

The product exhibited hypotensive activity in a standard test procedure.

EXAMPLE 7

1-[1-(2-[3-Indolyl]ethyl)piperid-4-yl]-3-[2-trifluoromethylphenyl]urea

Using the procedure of Example 1 4-amino-1-[2-(3-indolyl)ethyl]piperidine, hydrate (1.307 g.) and 2-trifluoromethylpheny isocyanate (0.982 g., 5% excess) gave the title compound as the hydrochloride (1.835 g., 82%) m.p. 233.6° (dec)

$C_{23}H_{25}N_4O\cdot HCl$ requires: C, 59.18; H, 5.61; N, 12.00
Found: C, 59.28; H, 5.79; N, 11.66%

The product exhibited marked hypotensive activity in a standard test procedure.

EXAMPLE 8

1-Benzoyl-3-[1-(2-[3-indolyl]ethyl)piperid-4-yl]urea

Using the procedure of Example 1 4-amino-1-[2-(3-indolyl)ethyl]piperidine, hydrate (1.307 g.) and benzoyl isocyanate (1.471 g.) gave the title compound as the hydrochloride (1.436 g., 63%). m.p. 248.0° (dec).

$C_{23}H_{26}N_4O_2\cdot HCl$ requires: C, 64.73; H, 6.38; N, 13.12.
Found: C, 64.43; H. 6.66; N, 13.11.

The product is an intermediate for the next Example and also exhibited marked hypotensive activity and good antihypertensive activity.

EXAMPLE 9

1-[1-(2-[3-Indolyl]ethyl)piperid-4-yl]urea 1-benzoyl-3-[1-(2-[3-indolyl]ethyl)piperid-4-yl]urea hydrochloride (1.180 g.) was refluxed in 2 N sodium hydroxide solution (20 ml) for 1 hour. The reaction mixture was cooled and the title compound was filtered off, (0.678 g., 86%) m.p. 212.2° (dec).

$C_{16}H_{22}N_4O$ requires: C, 67.10; H, 7.74; N, 19.57.
Found C, 67.56; H, 7.74; N, 19.35%.

The product exhibited hypotensive effects, but of short duration, at low doses in a standard test procedure. It also exhibited anti-hypertensive activity.

EXAMPLE 10

1-Phenyl-3-[1-(2-[3-indolyl]ethyl)piperid-4-yl] thiourea

4-Amino-1-[2-(3-indolyl)ethyl]piperidine hydrate (1.31 g, 0.005 mole) was dissolved in benzene (125 ml) and phenyl isothiocyanate (0.74 g, 0.0055 mole) added dropwise with stirring. After 24 hr., the mixture was filtered to give the title compound (free base) as a white amorphous solid (1.76 g). This was dissolved in a minimum of hot ethanol, saturated ethanol-HCl added until acid, and then the solution allowed to crystallise. Filtration afforded the title compound hydrochloride as colourless prisms (1.75 g), m.p. 224.8°.

Analysis Found: C, 63.67; H, 6.74; N, 13.32
$C_{22}H_{26}N_4S\cdot HCl$ requires C, 63.67; H, 6.56; N, 13.50%

The product exhibited hypotensive and anti-hypertensive activities.

EXAMPLE 11

1-(4-Chlorophenyl)-3[1-(2-[3-indolyl]ethyl)piperid-4-yl]thiourea

4-Amino-1-[2-(3-indolyl)ethyl]piperidine hydrate is treated with 4-chlorophenyl isothiocyanate in the manner described in Example 10 to obtain the title compound as the hydrochloride.

EXAMPLE 12

1-[3,4-Dichlorophenyl]-3-[1-(2-[3-indolyl]ethyl)piperid-4-yl]thiourea

4-Amino-1-[2-(3-indolyl)ethyl]piperidine hydrate is treated with 3,4-dichlorophenyl isothiocyanate in the manner described in Example 10 to obtain the title compound as the hydrochloride.

EXAMPLE 13

1-[4-Methoxyphenyl]-3[1-(2-[3-indolyl]ethyl)piperid-4-yl]thiourea

4-Amino-1-[2-(3-indolyl)ethyl] piperidine hydrate is treated with 4-methoxyphenyl isothiocyanate in the manner of Example 10 to obtain the title compound as the hydrochloride.

EXAMPLE 14

1-[3-Tolyl]-3-[1-(2-[3-indolyl]ethyl)piperid-4-yl]-thiourea

4-Amino-1-[2-(3-indolyl)ethyl]piperidine hydrate is treated with 3-tolyl isothiocyanate in the manner of Example 10 to obtain the title compound as the hydrochloride.

EXAMPLE 15

1-[2-Trifluoromethylphenyl]-3-[1-(2-[3-indolyl]ethyl)-piperid-4-yl]-thiourea

4-Amino-1-[2-(3-indolyl)ethyl]piperidine hydrate is treated with 2-trifluoromethylphenyl isothiocyanate in the manner of Example 10 to give the title compound as the hydrochloride.

EXAMPLE 16

1-[1-(2-[3-Indolyl]ethyl)piperid-4-yl]-3-cyclohexyl urea

4-Amino-1-[2-(3-indolyl)ethyl]piperidine, hydrate (1.307 g, 0.005 mole) in benzene (50 ml.) was treated with cyclohexyl isocyanate (0.688 g, 0.0055 mole) and the mixture stirred for 18 hrs. Filtration afforded the title compound as colourless prisms (1.893 g), m.p. 203.8°.

Analysis: Found: C, 71.74; H, 9.05; N, 14.91
$C_{22}H_{32}N_4O$ requires C, 71.70; H, 8.75; N. 15.21%

The product exhibited hypotensive activity.

EXAMPLE 17

1-[1-(2-[3-Indolyl]ethyl)piperid-4-yl]-3-(3-trifluoromethylphenyl)urea

3-[2-(4-Aminopiperidyl)ethyl]indole hydrate (1.31 g, 0.005 mole) was reacted with m-trifluoromethylphenyl isocyanate (1.03 g, 0.0055 mole) in the manner of Example 16 to give the title compound hydrochloride (0.87 g), m.p. 200.0°.

Found: C, 59.51; H, 5.84; N, 11.95 $C_{23}H_{25}F_3N_4O\cdot HCl$ requires C, 59.11; H, 5.57; N, 11.99%

The product exhibited hypotensive activity.

EXAMPLE 18

1-[1-(2-[3-Indolyl]ethyl)piperid-4-yl]-1-methyl-3-phenyl urea

3-[2-(4-Methylaminopiperidyl)ethyl]indole (1.28 g, 0.005 mole) and phenyl isocyanate (0.66 g, 0.0055 mole) were condensed in the manner of Example 16 to give the title compound hydrochloride (0.69 g), m.p. 217.6°.

Found: C, 65.85; H, 7.37; N, 13.03 $C_{23}H_{28}N_4O\cdot HCl\cdot \frac{1}{4}H_2O$ requires C, 66.17; H, 7.24; N, 13.42%

The product exhibited marked hypotensive activity.

EXAMPLE 19

1-[1-(2-[3-Indolyl]ethyl)piperid-4-yl]-1-methyl-3-phenyl thiourea

3-[2-(4-Methylaminopiperidyl)ethyl]indole (1.28 g, 0.005 mole) was stirred in dry benzene (75 ml) and treated with phenyl isothiocyanate (0.74 g, 0.0055 mole). Stirring was continued for 24 hr. and the mixture evaporated to give the title compound, which was converted to the hydrochloride by addition of hydrogen chloride in ethanol and precipitation with ether. Yield, 0.95 g, m.p. 193.7°.

Analysis: Found: C, 64.05; H, 6.99; N, 13.11 $C_{23}H_{28}N_4S.HCl$ requires C, 64.39; H, 6.81; N, 13.06%.

The product exhibited good hypotensive activity.

EXAMPLE 20

1-Benzoyl-3-[1-(2-[3-indolyl]ethyl)piperid-4-yl]thiourea

To a stirred solution of ammonium thiocyanate (2.28 g) in dry acetone (20 ml) was added a solution of benzoyl chloride (4.22 g) in dry acetone (20 ml). This mixture was stirred at 45° for 5 min. then treated with a solution of 3-[2-(4-aminopiperidyl)-ethyl]indole (7.84 g) in dry acetone (30 ml). After refluxing for 25 min., the mixture was cooled, poured into water (250 ml) and the liberated oil extracted into chloroform. Evaporation of the dried ($MgSO_4$) extract afforded the title compound which was crystallised from $EtOH-HCl/Et_2O$ as the hydrochloride (1.65 g), m.p. 212°–215°.

Found:- C, 61.70; H, 6.43; N, 12.14. $C_{23}H_{26}N_4OS$. HCl. ¼ $H_2O$ requires C, 61.74; H, 6.19; N, 12.52%.

The product exhibited hypotensive activity.

EXAMPLE 21

1-[1-(2-[3-Indolyl]ethyl)piperid-4-yl]thiourea

1-Benzoyl-3-[1-(2-[3-indolyl]ethyl)piperid-4-yl]-thiourea (2.21 g) was refluxed in water (20 ml) containing sodium hydroxide (1.0 g) for 5 min. The mixture was cooled and filtered to afford the title compound (1.59 g). Crystallisation from EtOH-HCl/ether afforded the hydrochloride (1.467 g), m.p. 228°–9°.

Found: C, 56.78; H, 7.20; N, 16.42 $C_{16}H_{22}N_4S$. HCl requires C, 56.70; H, 6.84; N, ;b 16.53%.

The product exhibited hypotensive activity.

EXAMPLE 22

1-Methyl-3-[1-(2-[3-indolyl]ethyl)piperid-4-yl]urea

Following the procedure of Example 1 3-[2-(4-aminopiperidyl) ethyl]indole is reacted with methyl isocyanate to give the title compound which is converted to the hydrochloride.

EXAMPLE 23

1-(2-Thienyl)-3-[1-(2-[3-indolyl]ethyl)piperidyl]thiourea

Following the procedure of Example 10 3-[2-(4-aminopiperidyl)ethyl]indole is treated with 2-thienyl isothiocyanate to give the title compound which is converted to the hydrochloride.

EXAMPLE 24

1-(2-Furyl)-3-[1-[3-indolyl]ethyl)piperidyl]urea

Following the procedure of Example 1 3-[1-(4-aminopiperidyl)ethyl]indole is treated with 2-furyl isocyanate to give the title compound which is converted to the hydrochloride.

EXAMPLE 25

1-Acetyl-3-[1-(2-[3-indolyl]ethyl)piperidyl]urea

3-[2-(4-Aminopiperidyl)ethyl]indole is treated with acetyl isocyanate following the procedure of Example 1 to give the title compound which is converted to the hydrochloride.

EXAMPLE 26

1-Cyclohexanoyl-3-[1-(2-[3-indolyl]ethyl)piperid-4-yl]urea

To a suspension of 1-[1-(2-[3-indolyl]ethyl)piperid-4-yl]urea (0.35 g) in dry benzene (2 ml) was added anhydrous pyridine (0.12 g) and then cyclohexanoyl chloride (0.18 g). After refluxing the mixture for 2 hours, the title compound was filtered off, washed, dried and converted in ethanolic hydrogen chloride to the hydrochloride (0.52 g) m.p. 236.3° C.

Analysis Found: C, 60.55; H, 7.59; N, 12.14%. $C_{23}H_{32}N_4O_2.HCl$ requires C, 60.64; H, 7.85; N, 12.30%.

The product exhibited very good hypotensive activity.

EXAMPLE 27

1-(2-Thienoyl)-3-[1-(2-[3-indolyl]-ethyl)-piperid-4-yl]urea

1-[1-(2-[3-Indolyl]ethyl)piperid-4-yl]urea (0.35 g) was treated with 2-thienoyl chloride (0.18 g) in the manner of Example 26 to give the title compound as the hydrochloride (0.13 g) m.p. 247.3° C.

Analysis Found: C, 56.76; H, 5.71; N, 12.67. $C_{21}H_{24}N_4O_2S.HCl$ requires C, 57.06; H, 5.93; N, 12.68%.

The product exhibited marked hypotensive activity.

We claim

1. A compound of general formula I

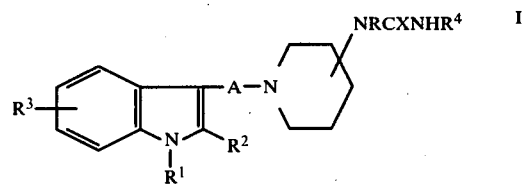

and pharmaceutically acceptable acid addition and quaternary ammonium salts thereof, wherein R represents hydrogen or lower alkyl, $R^1$ represents hydrogen or lower alkyl, $R^2$ represents hydrogen or lower alkyl, $R^3$ represents hydrogen, halogen, lower alkoxy, hydroxy, or lower alkyl, $R^4$ represents hydrogen, lower alkyl, cycloalkyl of 5 to 7 carbon atoms, thienyl, furyl, phenyl; phenyl mono- or disubstituted by halogen, lower alkyl, lower alkoxy, hydroxy or trifluoromethyl; or benzoyl, halobenzoyl, lower alkanoyl, cycloalkanoyl of 6 to 8 carbon atoms, or thienoyl, A represents an alkylene radical having from 1 to 5 carbon atoms and X is oxygen or sulphur.

2. A compound of the formula:

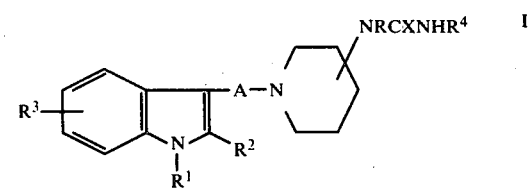

and pharmaceutically acceptable acid addition and quaternary ammonium salts thereof, wherein R represents hydrogen or lower alkyl, $R^1$ represents hydrogen or lower alkyl, $R^2$ represents hydrogen or lower alkyl, $R^3$ represents hydrogen, halogen, lower alkoxy, hydroxy, or lower alkyl, $R^4$ represents hydrogen, lower alkyl, phenyl; phenyl mono- or disubstituted by halogen, lower alkyl, lower alkoxy, hydroxy or trifluoromethyl; or lower alkanoyl, A represents an alkylene radical having from 1 to 5 carbon atoms and X is oxygen or sulphur.

3. A compound as claimed in claim 1, wherein $R^4$ is phenyl, o-trifluoromethyl-phenyl, benzoyl, cyclohexanoyl or cyclohexyl.

4. A compound as claimed in claim 1, wherein R is methyl.

5. A compound as claimed in claim 1, which is 1-phenyl-3-[1-(2-[indolyl]ethyl)piperid-4-yl]urea or a pharmaceutically acceptable acid addition salt thereof.

6. A compound as claimed in claim 1, which is 1-[1-(2-[3-indolyl]ethyl)piperid-4-yl]-3-[2-trifluoromethylphenyl]urea or a pharmaceutically acceptable acid addition salt thereof.

7. A compound as claimed in claim 1, which is 1-benzoyl-3-[1-(2-[3-indolyl]ethyl)piperid-4-yl]urea or a pharmaceutically acceptable acid addition salt thereof.

8. A compound as claimed in claim 1, which is 1-phenyl-3-[1-(2-[3-indolyl]ethyl)piperid-4-yl]-thiourea or a pharmaceutically acceptable acid addition salt thereof.

9. A compound as claimed in claim 1, which is 1-[1-(2-[3-indolyl]ethyl)piperid-4-yl]-1-methyl-3-phenyl urea or a pharmaceutically acceptable acid addition salt thereof.

10. A compound as claimed in claim 1, which is 1-[1-(2-[3-indolyl]ethyl)piperid-4-yl]-3-[3-tolyl]urea.

11. A compound as claimed in claim 1, which is 1-cyclohexanoyl-3-[1-(2-[3-indolyl]ethyl)-piperid-4-yl] urea or a pharmaceutically acceptable acid addition salt thereof.

12. A compound as claimed in claim 1, which is 1-(2-thienoyl)-3-[1-(2-[3-indolyl]-ethyl)-piperid-4-yl]urea or a pharmaceutically acceptable acid addition salt thereof.

13. A compound as claimed in claim 1, which is 1-[1-(2-[3-Indolyl]ethyl)piperid-4-yl]-1-methyl-3-phenyl thiourea or a pharmaceutically acceptable acid addition salt thereof.

14. A compound as claimed in claim 1, which is 1-[1-(2-[3-indolyl]ethyl)piperid-4-yl]thiourea or a pharmaceutically acceptable acid addition salt thereof.

15. A compound as claimed in claim 1, which is 1-[1-(2-[3-indolyl]ethyl)piperid-4-yl]-3-cyclohexyl urea or a pharmaceutically acceptable acid addition salt thereof.

16. A compound as claimed in claim 1, which is 1-[1-(2-[3-indolyl]ethyl)piperid-4-yl]-3-[4-methoxyphenyl] urea or a pharmaceutically acceptable acid addition salt thereof.

17. A pharmaceutical composition for use in treatment of the cardiovascular system which comprises a hypotensive amount of a compound of the formula:

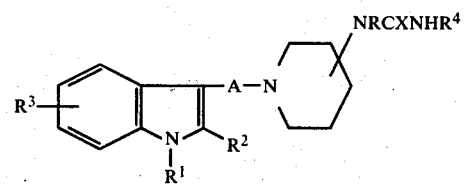

and pharmaceutically acceptable acid addition and quaternary ammonium salts thereof, wherein R represents hydrogen or lower alkyl, $R^1$ represents hydrogen or lower alkyl, $R^2$ represents hydrogen or lower alkyl, $R^3$ represents hydrogen, halogen, lower alkoxy, hydroxy, or lower alkyl, $R^4$ represents hydrogen, lower alkyl, cycloalkyl of 5 to 7 carbon atoms, thienyl, furyl, phenyl; phenyl mono- or disubstituted by halogen, lower alkyl, lower alkoxy, hydroxy or trifluoromethyl; or benzoyl, halobenzoyl, lower alkanoyl, cycloalkanoyl of 6 to 8 carbon atoms, or thieno A represents an alkylene radical having from 1 to 5 carbon atoms and X is oxygen or s and a pharmaceutically acceptable carrier.

18. A pharmaceutical composition for use in treatment of the cardiovascular system which comprises a hypotensive amount of a compound of the formula:

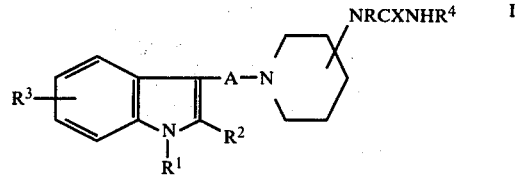

and pharmaceutically acceptable acid addition and quaternary ammonium salts thereof, wherein R represents hydrogen or lower alkyl, $R^1$ represents hydrogen or lower alkyl, $R^2$ represents hydrogen or lower alkyl, $R^3$ represents hydrogen, halogen, lower alkoxy, hydroxy, or lower alkyl, $R^4$ represents hydrogen, lower alkyl, phenyl; phenyl mono- or disubstituted by halogen, lower alkyl, lower alkoxy, hydroxy or trifluoromethyl; or lower alkanoyl, A represents an alkylene radical having from 1 to 5 carbon atoms and X is oxygen or sulphur, and a pharmaceutically acceptable carrier.

* * * * *